(12) United States Patent
de Waard

(10) Patent No.: US 6,746,837 B2
(45) Date of Patent: Jun. 8, 2004

(54) MULTIPLE DRUG RESISTANCE GENE ATRD OF ASPERGILLUS NIDULANS

(75) Inventor: Maarten A. de Waard, Wageningen (NL)

(73) Assignee: Stichting voor de Technische Wetenschappen, Utrecht (NL)

( * ) Notice: Subject to any disclaimer, the term of this patent is extended or adjusted under 35 U.S.C. 154(b) by 0 days.

(21) Appl. No.: 09/758,828

(22) Filed: Nov. 20, 2001

(65) Prior Publication Data

US 2002/0164772 A1 Nov. 7, 2002

Related U.S. Application Data

(62) Division of application No. 09/328,320, filed on Jun. 8, 1999, now Pat. No. 6,228,615, which is a division of application No. 08/996,545, filed on Dec. 23, 1997, now Pat. No. 5,928,898.

(51) Int. Cl.[7] .................. C12Q 1/00; C12Q 1/18; C12Q 1/26; C12P 21/06
(52) U.S. Cl. .................. 435/4; 435/6; 435/7.1; 435/7.2; 435/7.31; 435/193; 435/254.1; 435/254.21; 435/325; 435/362; 435/69.1; 435/320.1; 536/23.1; 536/23.74; 514/19; 424/25; 424/32; 424/189
(58) Field of Search .................. 435/4, 6, 7.1, 7.2, 435/7.3, 193, 254.1, 254.21, 320.1, 325, 362, 69.1, 25, 189, 32; 536/23.1, 23.74; 424/93.2, 93.5; 514/19

(56) References Cited

PUBLICATIONS

J. Darnell, *Molecular Cell Biology* pp. 107–108, 255–258 (1986).
Goodman, et al., *Goodman and Gilman's The Pharmacological Basis of Therapeutics* pp. 43–48, Eighth Edition (1990).
Hodges, et al., *Journal of Industrial Microbiology* vol. 13, pp 372–381 (1994).
Mackey, et al., *Analytical Biochemistry*, vol. 212, pp. 428–435 (1993).
G. Del Sorbo, et al. "Multidrug resistance in *Aspergillus nidulans* involves novel ATP–binding cassette transporters." *Mol. Gen. Genet.* vol. 254 pp417–426 (1997).
M.B. Tobin, et al. "Genes encoding multiple drug resistance–like proteins in *Aspergillus fumigatus* and *Aspergillus flavus*." *Gene* vol. 200, pp 11–23 (1997).
S.J. Thornewell, et al. "Cloning and characterization of CneMDR1: a *Cryptococcus neoformans* gene encoding a protein related to multidrug resistance proteins." *Gene* vol. 201, pp 21–29 (1997).
Xuei, et al., *Current Genetics*, vol. 26, pp. 225–227 (1994).

Primary Examiner—Lynette Smith
Assistant Examiner—Padma Baskar
(74) Attorney, Agent, or Firm—Stephen A. Slusher

(57) ABSTRACT

The invention provides isolated nucleic acid compounds encoding a multiple drug resistance protein of *Aspergillus nidulans*. Vectors and transformed host cells comprising the multiple drug resistance-encoding DNA of *Aspergillus nidulans* atrD are also provided. The invention further provides assays which utilize these transformed host cells.

3 Claims, No Drawings

US 6,746,837 B2

MULTIPLE DRUG RESISTANCE GENE ATRD OF ASPERGILLUS NIDULANS

This application is a divisional of, and claims the benefit of priority of, U.S. application Ser. No. 09/328,320 filed Jun. 8, 1999, now U.S. Pat. No. 6,228,615, which is a divisional of U.S. application Ser. No. 08/996,545 filed Dec. 23, 1997, now U.S. Pat. No. 5,928,898, the contents of each of which are herein incorporated by reference in their entirety.

TECHNICAL FIELD OF THE INVENTION

This invention relates to recombinant DNA technology. In particular, the invention concerns the cloning of nucleic acid encoding a multiple drug resistance protein of *Aspergillus nidulans*.

BACKGROUND OF THE INVENTION

Multiple drug resistance (MDR) mediated by the human mdr-1 gene product was initially recognized during the course of developing regimens for cancer chemotherapy (Fojo et al., 1987, *Journal of Clinical Oncology* 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leishmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, antiarrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62:385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have been designed to discover anti-Candida compounds. During development of antifungal agents, activity has generally been optimized based on activity against *Candida albicans*. As a consequence, these anti-Candida compounds frequently do not possess clinically significant activity against other fungal species such as *Aspergillus nidulans*. However, it is interesting to note that at higher concentrations some anti-Candida compounds are able to kill other fungal species such as *A. nidulans* and *A. fumigatus*. This type of observation suggests that the antifungal target(s) of these anti-Candida compounds is present in *A. nidulans* as well. Such results indicate that *A. nidulans* may possess a natural mechanism of resistance that permits them to survive in clinically relevant concentrations of antifungal compounds. Until the present invention, such a general mechanism of resistance to antifungal compounds in *A. nidulans* has remained undescribed.

SUMMARY OF THE INVENTION

The invention provides, inter alia, isolated nucleic acid molecules that comprise nucleic acid encoding a multiple drug resistance protein from Aspergillus nidulans, herein referred to as atrD, vectors encoding atrD, and host cells transformed with these vectors.

In another embodiment, the invention provides a method for determining the fungal MDR inhibition activity of a compound which comprises:
 a) placing a culture of fungal cells, transformed with a vector capable of expressing atrD, in the presence of:
  (i) an antifungal agent to which said fungal cell is resistant, but to which said fungal cell is sensitive in its untransformed state;
  (ii) a compound suspected of possessing fungal MDR inhibition activity; and
 b) determining the fungal MDR inhibition activity of said compound by measuring the ability of the antifungal agent to inhibit the growth of said fungal cell.

In still another embodiment the present invention relates to strains of *A. nidulans* in which the atrD gene is disrupted or otherwise mutated such that the atrD protein is not produced in said strains.

In yet another embodiment, the present invention relates to a method for identifiying new antifungal compounds comprising the use of atrD gene disruption or gene replacement strains of *A. nidulans*.

DETAILED DESCRIPTION OF THE INVENTION

The present invention provides isolated nucleic acid molecules that comprise a nucleic acid sequence encoding atrD. The cDNA (complementary deoxyribonucleic acid) sequence encoding atrD is provided in the Sequence Listing as SEQ ID NO: 1. The amino acid sequence of the protein encoded by atrD is provided in the Sequence Listing as SEQ ID NO: 2.

Those skilled in the art will recognize that the degenerate nature of the genetic code enables one to construct many different nucleic acid sequences that encode the amino acid sequence of SEQ ID NO: 2. The cDNA sequence depicted by SEQ ID NO: 1 is only one of many possible atrD-encoding sequences. Consequently, the constructions described below and in the accompanying examples for the preferred nucleic acid molecules, vectors, and transformants of the invention are illustrative and are not intended to limit the scope of the invention.

All nucleotide and amino acid abbreviations used in this disclosure are those accepted by the United States Patent and Trademark Office as set forth in 37 C.F.R. §1.822(b)(1994).

The term "vector" refers to any autonomously replicating or integrating agent, including but not limited to plasmids, cosmids, and viruses (including phage), comprising a nucleic acid molecule to which one or more additional nucleic acid molecules can be added. Included in the definition of "vector" is the term "expression vector". Vectors are used either to amplify and/or to express deoxyribonucleic acid (DNA), either genomic or cDNA, or RNA (ribonucleic acid) which encodes atrD, or to amplify DNA or RNA that hybridizes with DNA or RNA encoding atrD.

The term "expression vector" refers to vectors which comprise a transcriptional promoter (hereinafter "promoter") and other regulatory sequences positioned to drive expression of a DNA segment that encodes atrD. Expression vectors of the present invention are replicable DNA constructs in which a DNA sequence encoding atrD is operably linked to suitable control sequences capable of effecting the expression of atrD in a suitable host. Such control sequences include a promoter, an optional operator sequence to control transcription, a sequence encoding suitable MRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, atrD may be synthesized by host cells transformed with vectors that provide for the expression of DNA encoding atrD. The DNA encoding atrD may be the natural sequence or a synthetic sequence or a combination of both ("semi-synthetic sequence"). The in vitro or in vivo transcription and translation of these sequences results in the production of atrD. Synthetic and semi-synthetic sequences encoding atrD may be constructed by techniques well known in the art. See Brown et al. (1979) *Methods in Enzymology*, Academic Press, N.Y., 68:109–151. atrD-encoding DNA, or portions thereof, may be generated using a conventional DNA synthesizing apparatus such as the Applied Biosystems Model 380A,380B, 394 or 3948 DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences may be constructed which encode atrD. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al., Molecular Cloning: *A Laboratory Manual*, Cold Spring Harbor Press, Cold Spring Harbor Laboratory, Cold Spring Harbor, N.Y. (1989), or *Current Protocols in Molecular Biology* (F. M. Ausubel et al., 1989 and supplements). The contents of both of these references are incorporated herein by reference.

In another aspect, this invention provides the cDNA encoding atrD, which may be obtained by synthesizing the desired portion of SEQ ID NO:1 or by following the procedure carried out by Applicants. This procedure involved construction of a cosmid genomic DNA library from *Aspergillus nidulans* strain OC-1, a mutant derived from A42355. This library was screened for genes related to MDRs using a homologous probe generated by PCR. Degenerate PCR primers directed towards amplification of DNA sequences encoding highly conserved regions found in the ATP-binding domain of several MDR genes were synthesized. PCR using these primers and *Aspergillus nidulans* genomic DNA as template produced an approximately 400 base pair DNA fragment. The DNA sequence of this fragment was highly homologous to the ATP-binding region of several MDRs as predicted. This fragment was used as a hybridization probe to identify cosmid clones containing the entire atrD gene. A subclone from one such cosmid containing the entire atrD gene was sequenced to ascertain the entire sequence of atrD.

To effect the translation of atrD-encoding mRNA, one inserts the natural, synthetic, or semi-synthetic atrD-encoding DNA sequence into any of a large number of appropriate expression vectors through the use of appropriate restriction endonucleases and DNA ligases. Synthetic and semi-synthetic atrD-encoding DNA sequences can be designed, and natural atrD-encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the atrD-encoding DNA with the control sequences to achieve proper in-frame transcription and translation of the atrD molecule. The atrD-encoding DNA must be positioned so as to be in proper reading frame with the promoter and ribosome binding site of the expression vector, both of which are functional in the host cell in which atrD is to be expressed.

Expression of atrD in fungal cells, such as *Saccharomyces cerevisiae* is preferred. Suitable promoter sequences for use with yeast hosts include the promoters for 3-phosphoglycerate kinase (found on plasmid pAP12BD (ATCC 53231) and described in U.S. Pat. No. 4,935,350, Jun. 19, 1990) or other glycolytic enzymes such as enolase (found on plasmid pAC1 (ATCC 39532)), glyceraldehyde-3-phosphate dehydrogenase (derived from plasmid pHc-GAPC1 (ATCC 57090, 57091)), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV (ATCC 39475), U.S. Pat. No. 4,840, 896), glyceraldehyde 3-phosphate dehydrogenase, and enzymes responsible for maltose and galactose utilization (GAL1 found on plasmid pRY121 (ATCC 37658) and on plasmid pPST5, described below). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYCI promoter on plasmid YEpsec—hI1beta, ATCC 67024), also are advantageously used with yeast promoters.

A variety of expression vectors useful in the present invention are well known in the art. For expression in Saccharomyces, the plasmid YRp7, for example, (ATCC-40053, Stinchcomb et al., 1979, Nature 282:39; Kingsman et al., 1979, *Gene* 7:141; Tschemper et al., 1980, *Gene* 10:157) is commonly used. This plasmid contains the trp gene which provides a selection marker for a mutant strain of yeast lacking the ability to grow in tryptophan, for example ATCC 44076 or PEP4-1 (Jones, 1977, *Genetics* 85:12).

Expression vectors useful in the expression of atrD can be constructed by a number of methods. For example, the cDNA sequence encoding atrD can be synthesized using DNA synthesis techniques such as those described above. Such synthetic DNA can be synthesized to contain cohesive ends that allow facile cloning into an appropriately digested expression vector. For example, the cDNA encoding atrD can be synthesized to contain NotI cohesive ends. Such a synthetic DNA fragment can be ligated into a NotI-digested expression vector such as pYES-2 (Invitrogen Corp., San Diego Calif. 92121).

An expression vector can also be constructed in the following manner. Logarithmic phase *Aspergillus nidulans* cells are disrupted by grinding under liquid nitrogen according to the procedure of Minuth et al., 1982 (*Current Genetics* 5:227–231). *Aspergillus nidulans* mRNA is preferably isolated from the disrupted cells using the QuickPrep® mRNA Purification Kit (Pharmacia Biotech) according to the instructions of the manufacturer. cDNA is produced from the isolated mRNA using the TimeSaver® cDNA Synthesis Kit (Pharmacia Biotech) using oligo (dT) according to the procedure described by the manufacturer. In this process an EcoRI/NotI adapter (Stratagene, Inc.) is ligated to each end of the double stranded cDNA. The adapter modified cDNA is ligated into the vector Lambda Zap$^R$II® using the Predigested Lambda Zap$^R$II®/EcoRI/CIAP Cloning Kit (Stratagene, Inc.) according to the instructions of the manufacturer to create a cDNA library.

The library is screened for full-length cDNA encoding atrD using a $^{32}$P-radiolabeled fragment of the atrD gene. In this manner, a full-length cDNA clone is recovered from the *Aspergillus nidulans* cDNA library. A full-length cDNA clone recovered from the library is removed from the Lambda Zap$^R$II® vector by digestion with the restriction endonuclease NotI which produces a DNA fragment encoding atrD. The atrD encoding fragment is subcloned into plasmid pYES2 for expression studies. In this plasmid the atrD gene is operably linked to the *Saccharomyces cerevisiae* GAL1 promoter at the 5' end, and the yeast cyc1 transcription terminator at the 3' end. This plasmid further comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. The expression plasmid further comprises the yeast 2μ origin of replication (2μ ori) allowing replication in yeast host cells, the yeast URA3 gene for selection of *S. cerevisiae* cells transformed with the plasmid grown in a medium lacking uracil, and the origin of replication from the f1 filamentous phage.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as Saccharomyces cerevisiae cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

Nucleic acid, either RNA or DNA, which encodes atrD, or a portion thereof, is also useful in producing nucleic acid molecules useful in diagnostic assays for the detection of atrD MRNA, atrD cDNA, or atrD genomic DNA. Further, nucleic acid, either RNA or DNA, which does not encode atrD, but which nonetheless is capable of hybridizing with atrD-encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify atrD vectors and transformants and in in vitro diagnosis to detect atrD-like mRNA, CDNA, or genomic DNA from other organisms.

U.S. patent application Ser. No. 08/111,680 (now abandoned), the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with *Aspergillus nidulans* MDR inhibition activity. Host cells that express atrD provide an excellent means for the identification of compounds useful as inhibitors of *Aspergillus nidulans* MDR activity. Generally, the assay utilizes a culture of a yeast cell transformed with a vector which provides expression of atrD. The expression of atrD by the host cell enables the host cell to grow in the presence of an antifungal compound to which the yeast cell is sensitive to in the untransformed state. Thus, the transformed yeast cell culture is grown in the presence of i) an antifungal agent to which the untransformed yeast cell is sensitive, but to which the transformed host cell is resistant, and ii) a compound that is suspected of being an MDR inhibitor. The effect of the suspected MDR inhibitor is measured by testing for the ability of the antifungal compound to inhibit the growth of the transformed yeast cell. Such inhibition will occur if the suspected *Aspergillus nidulans* MDR inhibitor blocks the ability of atrD to prevent the antifungal compound from acting on the yeast cell. An illustrative example of such an assay is provided in Example 3.

In order to illustrate more fully the operation of this invention, the following examples are provided, but are not to be construed as a limitation on the scope of the invention.

EXAMPLE 1

Source of the atrD-Encoding Genomic DNA and cDNA of *Aspergillus nidulans*

Genomic DNA encoding atrD, or the corresponding cDNA sequence (presented in SEQ ID NO:1), may be from a natural sequence, a synthetic source or a combination of both ("semi-synthetic sequence"). The in vitro or in vivo transcription and translation of these sequences results in the production of atrD. Synthetic and semi-synthetic sequences encoding atrD may be constructed by techniques well known in the art. See Brown et al. (1979) *Methods in Enzymology*, Academic Press, N.Y., 68:109–151. atrD-encoding DNA, or portions thereof, may be generated using a conventional DNA synthesizing apparatus such as the Applied Biosystems Model 380A, 380B, 384 or 3848 DNA synthesizers (commercially available from Applied Biosystems, Inc., 850 Lincoln Center Drive, Foster City, Calif. 94404). The polymerase chain reaction is especially useful in generating these DNA sequences. PCR primers are constructed which include the translational start (ATG) and translational stop codon (TAG) of atrD. Restriction enzyme sites may be included on these PCR primers outside of the atrD coding region to facilitate rapid cloning into expression vectors. *Aspergillus nidulans* genomic DNA is used as the PCR template for synthesis of atrD including introns which is useful for expression studies in closely related fungi. In contrast, cDNA is used as the PCR template for synthesis of atrD devoid of introns which is useful for expression in foreign hosts such as *Saccharomyces cerevisiae* or bacterial hosts such as *Escherichia coli*.

EXAMPLE 2

Expression of the atrD Protein

*Saccharomyces cerevisiae* INVSc1 cells (Invitrogen Corp., San Diego Calif. 92191) are transformed with the plasmid containing atrD by the technique described by J. D. Beggs, 1988, *Nature* 275:104–109). The transformed yeast cells are grown in a broth medium containing YNB/CSM-Ura/raf (YNB/CSM-Ura [Yeast Nitrogen Base (Difco Laboratories, Detroit, Mich.) supplemented with CSM-URA (Bio 101, Inc.)] supplemented with 4% raffinose) at 28° C. in a shaker incubator until the culture is saturated. To induce expression of atrD, a portion of the culture is used to inoculate a flask containing YNB/CSM-Ura medium supplemented with 2% galactose (YNB/CSM-Ura/gal) rather than raffinose as the sole carbon source. The inoculated flask is incubated at 28° C. for about 16 hours.

EXAMPLE 3

Antifungal Potentiator Assay

Approximately $1 \times 10^6$ cells of a *Saccharomyces cerevisiae* INVSc1 culture expressing atrD are delivered to each of several agar plates containing YNB/CSM-Ura/gal. The agar surface is allowed to dry in a biohazard hood.

An antifungal compound that the untransformed yeast cell is typically sensitive to is dissolved in an appropriate solvent at a concentration that is biologically effective. Twenty µl of the solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the transformed *Saccharomyces cerevisiae* INVSc1 cells.

Compounds to be tested for the ability to inhibit atrD are dissolved in dimethylsulfoxide (DMSO). The amount of compound added to the DMSO depends on the solubility of the individual compound to be tested. Twenty µl of the suspensions containing a compound to be tested are delivered to an antibiotic susceptibility test disc (Difco Laboratories, Detroit, Mich.). The disc is then placed on the surface of the dried petri plates containing the transformed *Saccharomyces cerevisiae* INVSc1 cells approximately 2 cm from the antifungal-containing disc. Petri plates containing the two discs are incubated at 28° C. for about 16–48 hours.

Following this incubation period, the petri plates are examined for zones of growth inhibition around the discs. A zone of growth inhibition near the antifungal disc on the test plate indicates that the compound being tested for MDR inhibition activity blocks the activity of atrD and allows the antifungal compound to inhibit the growth of the yeast host cell. Such compounds are said to possess MDR inhibition activity. Little or no zone of growth inhibition indicates that the test compound does not block MDR activity and, thus, atrD is allowed to act upon the antifungal compound to prevent its activity upon the host cell.

EXAMPLE 4

Screen For Novel Antifungal Compounds

A plasmid molecule is constructed which contains DNA sequence information required for replication and genetic transformation in *E. coli* (e.g. ampicillin resistance). The plasmid also comprises DNA sequences encoding a marker for selection in fungal cells (e.g. hygromycin B phosphotransferase, phleomycin resistance, G418 resistance) under the control of an *A. nidulans* promoter. Additionally, the plasmid contains an internal portion of the atrD gene (e.g. about 3000 base pairs which lack 500 base pairs at the N-terminal end, and about 500 base pairs at the C-terminal end of the coding region specified by SEQ ID NO:1). The atrD gene fragment enables a single crossover gene disruption when transformed or otherwise introduced into *A. nidulans*.

Alternatively, a 5 kilobase pair to 6 kilobase pair region of *A. nidulans* genomic DNA containing the atrD gene is subcloned into the aforementioned plasmid. Then, a central portion of the atrD gene is removed and replaced with a selectable marker, such as hyromycin B phosphotransferase, for a double crossover gene replacement.

Gene disruption and gene replacement procedures for *A. nidulans* are well known in the art (See e.g. May et al, *J. Cell Biol.* 101, 712, 1985; Jones and Sealy-Lewis, *Curr. Genet.* 17, 81, 1990). Transformants are recovered on an appropriate selection medium, for example, hygromycin (if hygromycin B gene is used in the construction of disruption cassette). Gene replacement, or gene disruption, is verified by any suitable method, for example, by Southern blot hybridization.

Gene disruption or gene replacement strains are rendered hypersensitive to antifungal compounds, and are useful in screens for new antifungal compounds in whole cell growth inhibition studies.

I claim:

1. A method for determining the fungal multiple drug resistance (MDR) inhibition activity of a compound which comprises:
   a) placing a culture of fungal cells, transformed with a vector which expresses a nucleic acid encoding an atrD protein consisting essentially of the amino acid sequence of SEQ ID NO:2, in the presence of:
      (i) an antifungal agent to which said fungal cell is resistant, but to which said fungal cell is sensitive in its untransformed state;
      (ii) a compound suspected of possessing *Aspergillus nidulans* MDR inhibition activity; and
   b) determining the fungal MDR inhibition activity of said compound by measuring the ability of the antifungal agent to inhibit the growth of said fungal cell.

2. The method of claim 1 wherein the fungal cell is *Saccharomyces cerevisiae*.

3. The method of claim 1 wherein the culture of fungai cells is transformed with a vector which expresses a nucleic acid encoding an atrD protein of the amino acid sequence of SEQ ID NO:2.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 4002 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..4002

(xi) SEQUENCE DESCRIPTION: SEQ ID NO: 1:

```
ATG TCC CCG CTA GAG ACA AAT CCC CTT TCG CCA GAG ACT GCT ATG CGC        48
Met Ser Pro Leu Glu Thr Asn Pro Leu Ser Pro Glu Thr Ala Met Arg
 1               5                  10                  15

GAA CCT GCT GAG ACT TCA ACG ACG GAG GAG CAA GCT TCT ACA CCA CAC        96
Glu Pro Ala Glu Thr Ser Thr Thr Glu Glu Gln Ala Ser Thr Pro His
                20                  25                  30

GCT GCG GAC GAG AAG AAA ATC CTC AGC GAC CTC TCG GCT CCA TCT AGT       144
Ala Ala Asp Glu Lys Lys Ile Leu Ser Asp Leu Ser Ala Pro Ser Ser
            35                  40                  45

ACT ACA GCA ACC CCC GCA GAC AAG GAG CAC CGT CCT AAA TCG TCG TCC       192
Thr Thr Ala Thr Pro Ala Asp Lys Glu His Arg Pro Lys Ser Ser Ser
 50                  55                  60

AGC AAT AAT GCG GTC TCG GTC AAC GAA GTC GAT GCG CTT ATT GCG CAC       240
Ser Asn Asn Ala Val Ser Val Asn Glu Val Asp Ala Leu Ile Ala His
 65                  70                  75                  80

CTG CCA GAA GAC GAG AGG CAG GTC TTG AAG ACG CAG CTG GAG GAG ATC       288
Leu Pro Glu Asp Glu Arg Gln Val Leu Lys Thr Gln Leu Glu Glu Ile
                85                  90                  95

AAA GTA AAC ATC TCC TTC TTC GGT CTC TGG CGG TAT GCA ACA AAG ATG       336
Lys Val Asn Ile Ser Phe Phe Gly Leu Trp Arg Tyr Ala Thr Lys Met
                100                 105                 110

GAT ATA CTT ATC ATG GTA ATC AGT ACA ATC TGT GCC ATT GCT GCC GCG       384
Asp Ile Leu Ile Met Val Ile Ser Thr Ile Cys Ala Ile Ala Ala Ala
            115                 120                 125

TCG ACT TTC CAG AGG ATA ATG TTA TAT CAA ATC TCG TAC GAC GAG TTC       432
Ser Thr Phe Gln Arg Ile Met Leu Tyr Gln Ile Ser Tyr Asp Glu Phe
130                 135                 140

TAT GAT GAA TTG ACC AAG AAC GTA CTG TAC TTC GTA TAC CTC GGT ATC       480
Tyr Asp Glu Leu Thr Lys Asn Val Leu Tyr Phe Val Tyr Leu Gly Ile
145                 150                 155                 160

GGC GAG TTT GTC ACT GTC TAT GTT AGT ACT GTT GGC TTC ATC TAT ACC       528
Gly Glu Phe Val Thr Val Tyr Val Ser Thr Val Gly Phe Ile Tyr Thr
                165                 170                 175

GGA GAA CAC GCC ACG CAG AAG ATC CGC GAG TAT TAC CTT GAG TCT ATC       576
Gly Glu His Ala Thr Gln Lys Ile Arg Glu Tyr Tyr Leu Glu Ser Ile
                180                 185                 190

CTG CGC CAG AAC ATT GGC TAT TTT GAT AAA CTC GGT GCC GGG GAA GTG       624
Leu Arg Gln Asn Ile Gly Tyr Phe Asp Lys Leu Gly Ala Gly Glu Val
            195                 200                 205
```

```
ACC ACC CGT ATA ACA GCC GAT ACA AAC CTT ATC CAG GAT GGC ATT TCG      672
Thr Thr Arg Ile Thr Ala Asp Thr Asn Leu Ile Gln Asp Gly Ile Ser
    210             215             220

GAG AAG GTC GGT CTC ACT TTG ACT GCC CTG GCG ACA TTC GTG ACA GCA      720
Glu Lys Val Gly Leu Thr Leu Thr Ala Leu Ala Thr Phe Val Thr Ala
225             230             235             240

TTC ATT ATC GCC TAC GTC AAA TAC TGG AAG TTG GCT CTA ATT TGC AGC      768
Phe Ile Ile Ala Tyr Val Lys Tyr Trp Lys Leu Ala Leu Ile Cys Ser
            245             250             255

TCA ACA ATT GTG GCC CTC GTT CTC ACC ATG GGC GGT GGT TCT CAG TTT      816
Ser Thr Ile Val Ala Leu Val Leu Thr Met Gly Gly Gly Ser Gln Phe
        260             265             270

ATC ATC AAG TAC AGC AAA AAG TCG CTT GAC AGC TAC GGT GCA GGC GGC      864
Ile Ile Lys Tyr Ser Lys Lys Ser Leu Asp Ser Tyr Gly Ala Gly Gly
    275             280             285

ACT GTT GCG GAA GAG GTC ATC AGC TCC ATC AGA AAT GCC ACA GCG TTT      912
Thr Val Ala Glu Glu Val Ile Ser Ser Ile Arg Asn Ala Thr Ala Phe
290             295             300

GGC ACC CAA GAC AAG CTT GCG AAG CAG TAT GAG GTC CAC TTA GAC GAA      960
Gly Thr Gln Asp Lys Leu Ala Lys Gln Tyr Glu Val His Leu Asp Glu
305             310             315             320

GCT GAG AAA TGG GGA ACA AAG AAC CAG ATT GTC ATG GGT TTC ATG ATT     1008
Ala Glu Lys Trp Gly Thr Lys Asn Gln Ile Val Met Gly Phe Met Ile
            325             330             335

GGC GCC ATG TTT GGC CTT ATG TAC TCG AAC TAC GGT CTT GGC TTC TGG     1056
Gly Ala Met Phe Gly Leu Met Tyr Ser Asn Tyr Gly Leu Gly Phe Trp
        340             345             350

ATG GGT TCT CGT TTC CTG GTA GAT GGT GCA GTC GAT GTG GGT GAT ATT     1104
Met Gly Ser Arg Phe Leu Val Asp Gly Ala Val Asp Val Gly Asp Ile
    355             360             365

CTC ACA GTT CTC ATG GCC ATC TTG ATC GGA TCG TTC TCC TTG GGG AAC     1152
Leu Thr Val Leu Met Ala Ile Leu Ile Gly Ser Phe Ser Leu Gly Asn
370             375             380

GTT AGT CCA AAT GCT CAA GCA TTT ACA AAC GCT GTG GCC GCG GCC GCA     1200
Val Ser Pro Asn Ala Gln Ala Phe Thr Asn Ala Val Ala Ala Ala Ala
385             390             395             400

AAG ATA TTT GGA ACG ATC GAT CGC CAG TCC CCA TTA GAT CCA TAT TCG     1248
Lys Ile Phe Gly Thr Ile Asp Arg Gln Ser Pro Leu Asp Pro Tyr Ser
            405             410             415

AAC GAA GGG AAG ACG CTC GAC CAT TTT GAG GGC CAC ATT GAG TTA CGC     1296
Asn Glu Gly Lys Thr Leu Asp His Phe Glu Gly His Ile Glu Leu Arg
        420             425             430

AAT GTC AAG CAT ATT TAC CCA TCT AGA CCC GAG GTC ACC GTC ATG GAG     1344
Asn Val Lys His Ile Tyr Pro Ser Arg Pro Glu Val Thr Val Met Glu
    435             440             445

GAT GTT TCT CTG TCA ATG CCC GCT GGA AAA ACA ACC GCT TTA GTC GGC     1392
Asp Val Ser Leu Ser Met Pro Ala Gly Lys Thr Thr Ala Leu Val Gly
450             455             460

CCC TCT GGC TCT GGA AAA AGT ACG GTG GTC GGC TTG GTT GAG CGA TTC     1440
Pro Ser Gly Ser Gly Lys Ser Thr Val Val Gly Leu Val Glu Arg Phe
465             470             475             480

TAC ATG CCT GTT CGC GGT ACG GTT TTG CTG GAT GGC CAT GAC ATC AAG     1488
Tyr Met Pro Val Arg Gly Thr Val Leu Leu Asp Gly His Asp Ile Lys
            485             490             495

GAC CTC AAT CTC CGC TGG CTT CGC CAA CAG ATC TCT TTG GTT AGC CAG     1536
Asp Leu Asn Leu Arg Trp Leu Arg Gln Gln Ile Ser Leu Val Ser Gln
        500             505             510

GAG CCT GTT CTT TTT GGC ACG ACG ATT TAT AAG AAT ATT AGG CAC GGT     1584
Glu Pro Val Leu Phe Gly Thr Thr Ile Tyr Lys Asn Ile Arg His Gly
```

-continued

| | | | |
|---|---|---|---|
| 515 | | 520 | 525 |

CTC ATC GGC ACA AAG TAC GAG AAT GAA TCC GAG GAT AAG GTC CGG GAA    1632
Leu Ile Gly Thr Lys Tyr Glu Asn Glu Ser Glu Asp Lys Val Arg Glu
        530                 535                 540

CTC ATC GAG AAC GCG GCA AAA ATG GCG AAT GCT CAT GAC TTT ATT ACT    1680
Leu Ile Glu Asn Ala Ala Lys Met Ala Asn Ala His Asp Phe Ile Thr
545                 550                 555                 560

GCC TTG CCT GAA GGT TAT GAG ACC AAT GTT GGG CAG CGT GGC TTT CTC    1728
Ala Leu Pro Glu Gly Tyr Glu Thr Asn Val Gly Gln Arg Gly Phe Leu
                565                 570                 575

CTT TCA GGT GGC CAG AAA CAG CGC ATT GCA ATC GCC CGT GCC GTT GTT    1776
Leu Ser Gly Gly Gln Lys Gln Arg Ile Ala Ile Ala Arg Ala Val Val
                580                 585                 590

AGT GAC CCA AAA ATC CTG CTC CTG GAT GAA GCT ACT TCG GCC TTG GAC    1824
Ser Asp Pro Lys Ile Leu Leu Leu Asp Glu Ala Thr Ser Ala Leu Asp
            595                 600                 605

ACA AAA TCC GAA GGC GTG GTT CAA GCA GCT TTG GAG AGG GCA GCT GAA    1872
Thr Lys Ser Glu Gly Val Val Gln Ala Ala Leu Glu Arg Ala Ala Glu
        610                 615                 620

GGC CGA ACT ACT ATT GTG ATC GCT CAT CGC CTT TCC ACG ATC AAA ACG    1920
Gly Arg Thr Thr Ile Val Ile Ala His Arg Leu Ser Thr Ile Lys Thr
625                 630                 635                 640

GCG CAC AAC ATT GTG GTT CTG GTC AAT GGC AAA ATT GCT GAA CAA GGA    1968
Ala His Asn Ile Val Val Leu Val Asn Gly Lys Ile Ala Glu Gln Gly
                645                 650                 655

ACT CAC GAT GAA TTG GTT GAC CGC GGA GGC GCT TAT CGC AAA CTT GTG    2016
Thr His Asp Glu Leu Val Asp Arg Gly Gly Ala Tyr Arg Lys Leu Val
                660                 665                 670

GAG GCT CAA CGT ATC AAT GAA CAG AAG GAA GCT GAC GCC TTG GAG GAC    2064
Glu Ala Gln Arg Ile Asn Glu Gln Lys Glu Ala Asp Ala Leu Glu Asp
            675                 680                 685

GCC GAC GCT GAG GAT CTC ACG AAT GCA GAT ATT GCC AAA ATC AAA ACT    2112
Ala Asp Ala Glu Asp Leu Thr Asn Ala Asp Ile Ala Lys Ile Lys Thr
        690                 695                 700

GCG TCA AGC GCA TCA TCC GAT CTC GAC GGA AAA CCC ACA ACC ATT GAC    2160
Ala Ser Ser Ala Ser Ser Asp Leu Asp Gly Lys Pro Thr Thr Ile Asp
705                 710                 715                 720

CGC ACG GGC ACC CAC AAG TCT GTT TCC AGC GCG ATT CTT TCT AAA AGA    2208
Arg Thr Gly Thr His Lys Ser Val Ser Ser Ala Ile Leu Ser Lys Arg
                725                 730                 735

CCC CCC GAA ACA ACT CCG AAA TAC TCA TTA TGG ACG CTG CTC AAA TTT    2256
Pro Pro Glu Thr Thr Pro Lys Tyr Ser Leu Trp Thr Leu Leu Lys Phe
                740                 745                 750

GTT GCT TCC TTC AAC CGC CCT GAA ATC CCG TAC ATG CTC ATC GGT CTT    2304
Val Ala Ser Phe Asn Arg Pro Glu Ile Pro Tyr Met Leu Ile Gly Leu
            755                 760                 765

GTC TTC TCA GTG TTA GCT GGT GGT GGC CAA CCC ACG CAA GCA GTG CTA    2352
Val Phe Ser Val Leu Ala Gly Gly Gly Gln Pro Thr Gln Ala Val Leu
        770                 775                 780

TAT GCT AAA GCC ATC AGC ACA CTC TCG CTC CCA GAA TCA CAA TAT AGC    2400
Tyr Ala Lys Ala Ile Ser Thr Leu Ser Leu Pro Glu Ser Gln Tyr Ser
785                 790                 795                 800

AAG CTT CGA CAT GAT GCG GAT TTC TGG TCA TTG ATG TTC TTC GTG GTT    2448
Lys Leu Arg His Asp Ala Asp Phe Trp Ser Leu Met Phe Phe Val Val
                805                 810                 815

GGT ATC ATT CAG TTT ATC ACG CAG TCA ACC AAT GGT GCT GCA TTT GCC    2496
Gly Ile Ile Gln Phe Ile Thr Gln Ser Thr Asn Gly Ala Ala Phe Ala
                820                 825                 830

GTA TGC TCC GAG AGA CTT ATT CGT CGC GCG AGA AGC ACT GCC TTT CGG    2544

```
                    -continued

Val Cys Ser Glu Arg Leu Ile Arg Arg Ala Arg Ser Thr Ala Phe Arg
        835                 840                 845

ACG ATA CTC CGT CAA GAC ATT GCT TTC TTT GAC AAG GAA GAG AAT AGC    2592
Thr Ile Leu Arg Gln Asp Ile Ala Phe Phe Asp Lys Glu Glu Asn Ser
    850                 855                 860

ACC GGC GCT CTG ACC TCT TTC CTG TCC ACC GAG ACG AAG CAT CTC TCC    2640
Thr Gly Ala Leu Thr Ser Phe Leu Ser Thr Glu Thr Lys His Leu Ser
865                 870                 875                 880

GGT GTT AGC GGT GTG ACT CTA GGC ACG ATC TTG ATG ACC TCC ACG ACC    2688
Gly Val Ser Gly Val Thr Leu Gly Thr Ile Leu Met Thr Ser Thr Thr
                885                 890                 895

CTA GGA GCG GCT ATC ATT ATT GCC CTG GCG ATT GGG TGG AAA TTG GCC    2736
Leu Gly Ala Ala Ile Ile Ile Ala Leu Ala Ile Gly Trp Lys Leu Ala
                900                 905                 910

TTA GTT TGT ATC TCG GTT GTG CCG GTT CTC CTG GCA TGC GGT TTC TAC    2784
Leu Val Cys Ile Ser Val Val Pro Val Leu Leu Ala Cys Gly Phe Tyr
            915                 920                 925

CGA TTC TAT ATG CTA GCC CAG TTT CAA TCA CGC TCC AAG CTT GCT TAT    2832
Arg Phe Tyr Met Leu Ala Gln Phe Gln Ser Arg Ser Lys Leu Ala Tyr
        930                 935                 940

GAG GGA TCT GCA AAC TTT GCT TGC GAG GCT ACA TCG TCT ATC CGC ACA    2880
Glu Gly Ser Ala Asn Phe Ala Cys Glu Ala Thr Ser Ser Ile Arg Thr
945                 950                 955                 960

GTT GCG TCA TTA ACC CGG GAA AGG GAT GTC TGG GAG ATT TAC CAT GCC    2928
Val Ala Ser Leu Thr Arg Glu Arg Asp Val Trp Glu Ile Tyr His Ala
                965                 970                 975

CAG CTT GAC GCA CAA GGC AGG ACC AGT CTA ATC TCT GTC TTG AGG TCA    2976
Gln Leu Asp Ala Gln Gly Arg Thr Ser Leu Ile Ser Val Leu Arg Ser
                980                 985                 990

TCC CTG TTA TAT GCG TCG TCG CAG GCA CTT GTT TTC TTC TGC GTT GCG    3024
Ser Leu Leu Tyr Ala Ser Ser Gln Ala Leu Val Phe Phe Cys Val Ala
            995                 1000                1005

CTC GGG TTT TGG TAC GGA GGG ACA CTT CTT GGT CAC CAC GAG TAT GAC    3072
Leu Gly Phe Trp Tyr Gly Gly Thr Leu Leu Gly His His Glu Tyr Asp
        1010                1015                1020

ATT TTC CGC TTC TTT GTT TGT TTC TCC GAG ATT CTC TTT GGT GCT CAA    3120
Ile Phe Arg Phe Phe Val Cys Phe Ser Glu Ile Leu Phe Gly Ala Gln
1025                1030                1035                1040

TCC GCG GGC ACC GTC TTT TCC TTT GCA CCA GAC ATG GGC AAG GCG AAG    3168
Ser Ala Gly Thr Val Phe Ser Phe Ala Pro Asp Met Gly Lys Ala Lys
                1045                1050                1055

AAT GCG GCC GCC GAA TTC CGA CGA CTG TTC GAC CGA AAG CCA CAA ATT    3216
Asn Ala Ala Ala Glu Phe Arg Arg Leu Phe Asp Arg Lys Pro Gln Ile
                1060                1065                1070

GAT AAC TGG TCT GAA GAG GGC GAG AAG CTC GAA ACG GTG GAA GGT GAA    3264
Asp Asn Trp Ser Glu Glu Gly Glu Lys Leu Glu Thr Val Glu Gly Glu
            1075                1080                1085

ATC GAA TTT AGG AAC GTG CAC TTC AGA TAC CCG ACC CGC CCA GAA CAG    3312
Ile Glu Phe Arg Asn Val His Phe Arg Tyr Pro Thr Arg Pro Glu Gln
        1090                1095                1100

CCT GTC CTG CGC GGC TTG GAC CTG ACC GTG AAG CCT GGA CAA TAT GTT    3360
Pro Val Leu Arg Gly Leu Asp Leu Thr Val Lys Pro Gly Gln Tyr Val
1105                1110                1115                1120

GCG CTT GTC GGA CCC AGC GGT TGT GGC AAG AGT ACC ACC ATT GCA TTG    3408
Ala Leu Val Gly Pro Ser Gly Cys Gly Lys Ser Thr Thr Ile Ala Leu
                1125                1130                1135

CTT GAG CGC TTT TAC GAT GCG ATT GCC GGG TCC ATC CTT GTT GAT GGG    3456
Leu Glu Arg Phe Tyr Asp Ala Ile Ala Gly Ser Ile Leu Val Asp Gly
                1140                1145                1150
```

-continued

```
AAG GAC ATA AGT AAA CTA AAT ATC AAC TCC TAC CGC AGC TTT CTG TCA      3504
Lys Asp Ile Ser Lys Leu Asn Ile Asn Ser Tyr Arg Ser Phe Leu Ser
            1155                1160                1165

CTG GTC AGC CAG GAG CCG ACA CTG TAC CAG GGC ACC ATC AAG GAA AAC      3552
Leu Val Ser Gln Glu Pro Thr Leu Tyr Gln Gly Thr Ile Lys Glu Asn
        1170                1175                1180

ATC TTA CTT GGT ATT GTC GAA GAT GAC GTA CCG GAA GAA TTC TTG ATT      3600
Ile Leu Leu Gly Ile Val Glu Asp Asp Val Pro Glu Glu Phe Leu Ile
1185                1190                1195                1200

AAG GCT TGC AAG GAC GCT AAT ATC TAC GAC TTC ATC ATG TCG CTC CCG      3648
Lys Ala Cys Lys Asp Ala Asn Ile Tyr Asp Phe Ile Met Ser Leu Pro
                1205                1210                1215

GAG GGC TTT AAT ACA GTT GTT GGC AGC AAG GGA GGC ATG TTG TCT GGC      3696
Glu Gly Phe Asn Thr Val Val Gly Ser Lys Gly Gly Met Leu Ser Gly
            1220                1225                1230

GGC CAA AAG CAA CGT GTG GCC ATT GCC CGA GCC CTT CTT CGG GAT CCC      3744
Gly Gln Lys Gln Arg Val Ala Ile Ala Arg Ala Leu Leu Arg Asp Pro
        1235                1240                1245

AAA ATC CTT CTT CTC GAT GAA GCG ACG TCA GCC CTC GAC TCC GAG TCA      3792
Lys Ile Leu Leu Leu Asp Glu Ala Thr Ser Ala Leu Asp Ser Glu Ser
1250                1255                1260

GAA AAG GTC GTC CAG GCG GCT TTG GAT GCC GCT GCC CGA GGC CGA ACC      3840
Glu Lys Val Val Gln Ala Ala Leu Asp Ala Ala Ala Arg Gly Arg Thr
1265                1270                1275                1280

ACA ATC GCC GTT GCA CAC CGA CTC AGC ACG ATT CAA AAG GCG GAC GTT      3888
Thr Ile Ala Val Ala His Arg Leu Ser Thr Ile Gln Lys Ala Asp Val
                1285                1290                1295

ATC TAT GTT TTC GAC CAA GGC AAG ATC GTC GAA AGC GGA ACG CAC AGC      3936
Ile Tyr Val Phe Asp Gln Gly Lys Ile Val Glu Ser Gly Thr His Ser
            1300                1305                1310

GAA CTG GTC CAG AAA AAG GGC CGG TAC TAC GAG CTG GTC AAC TTG CAG      3984
Glu Leu Val Gln Lys Lys Gly Arg Tyr Tyr Glu Leu Val Asn Leu Gln
        1315                1320                1325

AGC TTG GGC AAG GGC CAT                                              4002
Ser Leu Gly Lys Gly His
    1330
```

(2) INFORMATION FOR SEQ ID NO: 2:

(i) SEQUENCE CHARACTERISTICS:
        (A) LENGTH: 1334 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Pro Leu Glu Thr Asn Pro Leu Ser Pro Glu Thr Ala Met Arg
 1               5                  10                  15

Glu Pro Ala Glu Thr Ser Thr Glu Glu Gln Ala Ser Thr Pro His
             20                  25                  30

Ala Ala Asp Glu Lys Lys Ile Leu Ser Asp Leu Ser Ala Pro Ser Ser
             35                  40                  45

Thr Thr Ala Thr Pro Ala Asp Lys Glu His Arg Pro Lys Ser Ser Ser
     50                  55                  60

Ser Asn Asn Ala Val Ser Val Asn Glu Val Asp Ala Leu Ile Ala His
 65                  70                  75                  80

Leu Pro Glu Asp Glu Arg Gln Val Leu Lys Thr Gln Leu Glu Glu Ile
                 85                  90                  95

Lys Val Asn Ile Ser Phe Phe Gly Leu Trp Arg Tyr Ala Thr Lys Met
```

-continued

```
                    100                 105                 110
Asp Ile Leu Ile Met Val Ile Ser Thr Ile Cys Ala Ile Ala Ala Ala
            115                 120                 125

Ser Thr Phe Gln Arg Ile Met Leu Tyr Gln Ile Ser Tyr Asp Glu Phe
    130                 135                 140

Tyr Asp Glu Leu Thr Lys Asn Val Leu Tyr Phe Val Tyr Leu Gly Ile
145                 150                 155                 160

Gly Glu Phe Val Thr Val Tyr Val Ser Thr Val Gly Phe Ile Tyr Thr
                165                 170                 175

Gly Glu His Ala Thr Gln Lys Ile Arg Glu Tyr Tyr Leu Glu Ser Ile
            180                 185                 190

Leu Arg Gln Asn Ile Gly Tyr Phe Asp Lys Leu Gly Ala Gly Glu Val
        195                 200                 205

Thr Thr Arg Ile Thr Ala Asp Thr Asn Leu Ile Gln Asp Gly Ile Ser
    210                 215                 220

Glu Lys Val Gly Leu Thr Leu Thr Ala Leu Ala Thr Phe Val Thr Ala
225                 230                 235                 240

Phe Ile Ile Ala Tyr Val Lys Tyr Trp Lys Leu Ala Leu Ile Cys Ser
                245                 250                 255

Ser Thr Ile Val Ala Leu Val Leu Thr Met Gly Gly Ser Gln Phe
            260                 265                 270

Ile Ile Lys Tyr Ser Lys Lys Ser Leu Asp Ser Tyr Gly Ala Gly Gly
        275                 280                 285

Thr Val Ala Glu Glu Val Ile Ser Ser Ile Arg Asn Ala Thr Ala Phe
    290                 295                 300

Gly Thr Gln Asp Lys Leu Ala Lys Gln Tyr Glu Val His Leu Asp Glu
305                 310                 315                 320

Ala Glu Lys Trp Gly Thr Lys Asn Gln Ile Val Met Gly Phe Met Ile
                325                 330                 335

Gly Ala Met Phe Gly Leu Met Tyr Ser Asn Tyr Gly Leu Gly Phe Trp
            340                 345                 350

Met Gly Ser Arg Phe Leu Val Asp Gly Ala Val Asp Val Gly Asp Ile
        355                 360                 365

Leu Thr Val Leu Met Ala Ile Leu Ile Gly Ser Phe Ser Leu Gly Asn
    370                 375                 380

Val Ser Pro Asn Ala Gln Ala Phe Thr Asn Ala Val Ala Ala Ala Ala
385                 390                 395                 400

Lys Ile Phe Gly Thr Ile Asp Arg Gln Ser Pro Leu Asp Pro Tyr Ser
                405                 410                 415

Asn Glu Gly Lys Thr Leu Asp His Phe Glu Gly His Ile Glu Leu Arg
            420                 425                 430

Asn Val Lys His Ile Tyr Pro Ser Arg Pro Glu Val Thr Val Met Glu
        435                 440                 445

Asp Val Ser Leu Ser Met Pro Ala Gly Lys Thr Thr Ala Leu Val Gly
    450                 455                 460

Pro Ser Gly Ser Gly Lys Ser Thr Val Val Gly Leu Val Glu Arg Phe
465                 470                 475                 480

Tyr Met Pro Val Arg Gly Thr Val Leu Leu Asp Gly His Asp Ile Lys
                485                 490                 495

Asp Leu Asn Leu Arg Trp Leu Arg Gln Gln Ile Ser Leu Val Ser Gln
            500                 505                 510

Glu Pro Val Leu Phe Gly Thr Thr Ile Tyr Lys Asn Ile Arg His Gly
        515                 520                 525
```

-continued

```
Leu Ile Gly Thr Lys Tyr Glu Asn Glu Ser Glu Asp Lys Val Arg Glu
    530                 535                 540
Leu Ile Glu Asn Ala Ala Lys Met Ala Asn Ala His Asp Phe Ile Thr
545                 550                 555                 560
Ala Leu Pro Glu Gly Tyr Glu Thr Asn Val Gly Gln Arg Gly Phe Leu
                565                 570                 575
Leu Ser Gly Gly Gln Lys Gln Arg Ile Ala Ile Ala Arg Ala Val Val
                580                 585                 590
Ser Asp Pro Lys Ile Leu Leu Asp Glu Ala Thr Ser Ala Leu Asp
                595                 600                 605
Thr Lys Ser Glu Gly Val Val Gln Ala Ala Leu Glu Arg Ala Ala Glu
    610                 615                 620
Gly Arg Thr Thr Ile Val Ile Ala His Arg Leu Ser Thr Ile Lys Thr
625                 630                 635                 640
Ala His Asn Ile Val Val Leu Val Asn Gly Lys Ile Ala Glu Gln Gly
                645                 650                 655
Thr His Asp Glu Leu Val Asp Arg Gly Gly Ala Tyr Arg Lys Leu Val
                660                 665                 670
Glu Ala Gln Arg Ile Asn Glu Gln Lys Glu Ala Asp Ala Leu Glu Asp
                675                 680                 685
Ala Asp Ala Glu Asp Leu Thr Asn Ala Asp Ile Ala Lys Ile Lys Thr
690                 695                 700
Ala Ser Ser Ala Ser Ser Asp Leu Asp Gly Lys Pro Thr Thr Ile Asp
705                 710                 715                 720
Arg Thr Gly Thr His Lys Ser Val Ser Ser Ala Ile Leu Ser Lys Arg
                725                 730                 735
Pro Pro Glu Thr Thr Pro Lys Tyr Ser Leu Trp Thr Leu Leu Lys Phe
                740                 745                 750
Val Ala Ser Phe Asn Arg Pro Glu Ile Pro Tyr Met Leu Ile Gly Leu
                755                 760                 765
Val Phe Ser Val Leu Ala Gly Gly Gln Pro Thr Gln Ala Val Leu
    770                 775                 780
Tyr Ala Lys Ala Ile Ser Thr Leu Ser Leu Pro Glu Ser Gln Tyr Ser
785                 790                 795                 800
Lys Leu Arg His Asp Ala Asp Phe Trp Ser Leu Met Phe Val Val
                805                 810                 815
Gly Ile Ile Gln Phe Ile Thr Gln Ser Thr Asn Gly Ala Ala Phe Ala
                820                 825                 830
Val Cys Ser Glu Arg Leu Ile Arg Arg Ala Arg Ser Thr Ala Phe Arg
                835                 840                 845
Thr Ile Leu Arg Gln Asp Ile Ala Phe Phe Asp Lys Glu Glu Asn Ser
    850                 855                 860
Thr Gly Ala Leu Thr Ser Phe Leu Ser Thr Glu Thr Lys His Leu Ser
865                 870                 875                 880
Gly Val Ser Gly Val Thr Leu Gly Thr Ile Leu Met Thr Ser Thr Thr
                885                 890                 895
Leu Gly Ala Ala Ile Ile Ile Ala Leu Ala Ile Gly Trp Lys Leu Ala
                900                 905                 910
Leu Val Cys Ile Ser Val Val Pro Val Leu Leu Ala Cys Gly Phe Tyr
                915                 920                 925
Arg Phe Tyr Met Leu Ala Gln Phe Gln Ser Arg Ser Lys Leu Ala Tyr
    930                 935                 940
```

-continued

```
Glu Gly Ser Ala Asn Phe Ala Cys Glu Ala Thr Ser Ser Ile Arg Thr
945                 950                 955                 960

Val Ala Ser Leu Thr Arg Glu Arg Asp Val Trp Glu Ile Tyr His Ala
                965                 970                 975

Gln Leu Asp Ala Gln Gly Arg Thr Ser Leu Ile Ser Val Leu Arg Ser
            980                 985                 990

Ser Leu Leu Tyr Ala Ser Ser Gln Ala Leu Val Phe Phe Cys Val Ala
        995                 1000                1005

Leu Gly Phe Trp Tyr Gly Gly Thr Leu Leu Gly His His Glu Tyr Asp
    1010                1015                1020

Ile Phe Arg Phe Phe Val Cys Phe Ser Glu Ile Leu Phe Gly Ala Gln
1025                1030                1035                1040

Ser Ala Gly Thr Val Phe Ser Phe Ala Pro Asp Met Gly Lys Ala Lys
                1045                1050                1055

Asn Ala Ala Ala Glu Phe Arg Arg Leu Phe Asp Arg Lys Pro Gln Ile
            1060                1065                1070

Asp Asn Trp Ser Glu Glu Gly Glu Lys Leu Glu Thr Val Glu Gly Glu
        1075                1080                1085

Ile Glu Phe Arg Asn Val His Phe Arg Tyr Pro Thr Arg Pro Glu Gln
    1090                1095                1100

Pro Val Leu Arg Gly Leu Asp Leu Thr Val Lys Pro Gly Gln Tyr Val
1105                1110                1115                1120

Ala Leu Val Gly Pro Ser Gly Cys Gly Lys Ser Thr Thr Ile Ala Leu
                1125                1130                1135

Leu Glu Arg Phe Tyr Asp Ala Ile Ala Gly Ser Ile Leu Val Asp Gly
            1140                1145                1150

Lys Asp Ile Ser Lys Leu Asn Ile Asn Ser Tyr Arg Ser Phe Leu Ser
        1155                1160                1165

Leu Val Ser Gln Glu Pro Thr Leu Tyr Gln Gly Thr Ile Lys Glu Asn
    1170                1175                1180

Ile Leu Leu Gly Ile Val Glu Asp Asp Val Pro Glu Glu Phe Leu Ile
1185                1190                1195                1200

Lys Ala Cys Lys Asp Ala Asn Ile Tyr Asp Phe Ile Met Ser Leu Pro
                1205                1210                1215

Glu Gly Phe Asn Thr Val Val Gly Ser Lys Gly Gly Met Leu Ser Gly
            1220                1225                1230

Gly Gln Lys Gln Arg Val Ala Ile Ala Arg Ala Leu Leu Arg Asp Pro
        1235                1240                1245

Lys Ile Leu Leu Leu Asp Glu Ala Thr Ser Ala Leu Asp Ser Glu Ser
    1250                1255                1260

Glu Lys Val Val Gln Ala Ala Leu Asp Ala Ala Ala Arg Gly Arg Thr
1265                1270                1275                1280

Thr Ile Ala Val Ala His Arg Leu Ser Thr Ile Gln Lys Ala Asp Val
                1285                1290                1295

Ile Tyr Val Phe Asp Gln Gly Lys Ile Val Glu Ser Gly Thr His Ser
            1300                1305                1310

Glu Leu Val Gln Lys Lys Gly Arg Tyr Tyr Glu Leu Val Asn Leu Gln
        1315                1320                1325

Ser Leu Gly Lys Gly His
    1330
```

(2) INFORMATION FOR SEQ ID NO: 3:

(i) SEQUENCE CHARACTERISTICS:

(A) LENGTH: 4002 base pairs
(B) TYPE: nucleic acid
(C) STRANDEDNESS: single
(D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO: 3:

```
AUGUCCCCGC UAGAGACAAA UCCCCUUUCG CCAGAGACUG CUAUGCGCGA ACCUGCUGAG      60
ACUUCAACGA CGGAGGAGCA AGCUUCUACA CCACACGCUG CGGACGAGAA GAAAAUCCUC     120
AGCGACCUCU CGGCUCCAUC UAGUACUACA GCAACCCCCG CAGACAAGGA GCACCGUCCU     180
AAAUCGUCGU CCAGCAAUAA UGCGGUCUCG GUCAACGAAG UCGAUGCGCU AUUGCGCAC      240
CUGCCAGAAG ACGAGAGGCA GGUCUUGAAG ACGCAGCUGG AGGAGAUCAA AGUAAACAUC     300
UCCUUCUUCG GUCUCUGGCG GUAUGCAACA AAGAUGGAUA UACUUAUCAU GGUAAUCAGU     360
ACAAUCUGUG CCAUUGCUGC CGCGUCGACU UUCCAGAGGA UAAUGUUAUA UCAAAUCUCG     420
UACGACGAGU CUAUGAUGA AUUGACCAAG AACGUACUGU ACUUCGUAUA CCUCGGUAUC      480
GGCGAGUUUG UCACUGUCUA UGUUAGUACU GUUGGCUUCA UCUAUACCGG AGAACACGCC     540
ACGCAGAAGA UCCGCGAGUA UUACCUUGAG UCUAUCCUGC GCCAGAACAU UGGCUAUUUU     600
GAUAAACUCG GUGCCGGGA AGUGACCACC CGUAUAACAG CCGAUACAAA CCUUAUCCAG      660
GAUGGCAUUU CGGAGAAGGU CGGUCUCACU UUGACUGCCC UGGCGACAUU CGUGACAGCA     720
UUCAUUAUCG CCUACGUCAA AUACUGGAAG UUGGCUCUAA UUUGCAGCUC AACAAUUGUG     780
GCCCUCGUUC UCACCAUGGG CGGUGGUUCU CAGUUUAUCA UCAAGUACAG CAAAAAGUCG     840
CUUGACAGCU ACGUGCAGG CGGCACUGUU GCGGAAGAGG UCAUCAGCUC CAUCAGAAAU      900
GCCACAGCGU UUGGCACCCA AGACAAGCUU GCGAAGCAGU AUGAGGUCCA CUUAGACGAA     960
GCUGAGAAAU GGGAACAAA GAACCAGAUU GUCAUGGGUU UCAUGAUUGG CGCCAUGUUU     1020
GGCCUUAUGU ACUCGAACUA CGGUCUUGGC UUCUGGAUGG GUUCUCGUUU CCUGGUAGAU    1080
GGUGCAGUCG AUGUGGGUGA UAUUCUCACA GUUCUCAUGG CCAUCUUGAU CGGAUCGUUC    1140
UCCUUGGGGA ACGUUAGUCC AAAUGCUCAA GCAUUUACAA ACGCUGUGGC CGCGGCCGCA    1200
AAGAUAUUUG GAACGAUCGA UCGCCAGUCC CCAUUAGAUC CAUAUUCGAA CGAAGGGAAG    1260
ACGCUCGACC AUUUUGAGGG CCACAUUGAG UUACGCAAUG UCAAGCAUAU UUACCCAUCU    1320
AGACCCGAGG UCACCGUCAU GGAGGAUGUU UCUCUGUCAA UGCCCGCUGG AAAAACAACC    1380
GCUUUAGUCG GCCCCUCUGG CUCUGGAAAA AGUACGGUGG UCGGCUUGGU UGAGCGAUUC    1440
UACAUGCCUG UUCGCGGUAC GGUUUUGCUG GAUGGCCAUG ACAUCAAGGA CCUCAAUCUC    1500
CGCUGGCUUC GCCAACAGAU CUCUUUGGUU AGCCAGGAGC CUGUUCUUUU UGGCACGACG    1560
AUUUAUAAGA AUAUUAGGCA CGGUCUCAUC GGCACAAAGU ACGAGAAUGA AUCCGAGGAU    1620
AAGGUCCGGG AACUCAUCGA GAACGCGGCA AAAAUGGCGA AUGCUCAUGA CUUUAUUACU    1680
GCCUUGCCUG AAGGUUAUGA GACCAAUGUU GGGCAGCGUG GCUUUCUCCU UUCAGGUGGC    1740
CAGAAACAGC GCAUUGCAAU CGCCCGUGCC GUUGUUAGUG ACCCAAAAAU CCUGCUCCUG    1800
GAUGAAGCUA CUUCGGCCUU GGACACAAAA UCCGAAGGCG UGGUUCAAGC AGCUUUGGAG    1860
AGGGCAGCUG AAGGCCGAAC UACUAUUGUG AUCGCUCAUC GCCUUUCCAC GAUCAAAACG    1920
GCGCACAACA UUGUGGUUCU GGUCAAUGGC AAAAUUGCUG AACAAGGAAC UCACGAUGAA    1980
```

| | |
|---|---|
| UUGGUUGACC GCGGAGGCGC UUAUCGCAAA CUUGUGGAGG CUCAACGUAU CAAUGAACAG | 2040 |
| AAGGAAGCUG ACGCCUUGGA GGACGCCGAC GCUGAGGAUC UCACGAAUGC AGAUAUUGCC | 2100 |
| AAAAUCAAAA CUGCGUCAAG CGCAUCAUCC GAUCUCGACG GAAAACCCAC AACCAUUGAC | 2160 |
| CGCACGGGCA CCCACAAGUC UGUUUCCAGC GCGAUUCUUU CUAAAAGACC CCCCGAAACA | 2220 |
| ACUCCGAAAU ACUCAUUAUG GACGCUGCUC AAAUUUGUUG CUUCCUUCAA CCGCCCUGAA | 2280 |
| AUCCCGUACA UGCUCAUCGG UCUUGUCUUC UCAGUGUUAG CUGGUGGUGG CCAACCCACG | 2340 |
| CAAGCAGUGC UAUAUGCUAA AGCCAUCAGC ACACUCUCGC UCCCAGAAUC ACAAUAUAGC | 2400 |
| AAGCUUCGAC AUGAUGCGGA UUUCUGGUCA UUGAUGUUCU UCGUGGUUGG UAUCAUUCAG | 2460 |
| UUUAUCACGC AGUCAACCAA UGGUGCUGCA UUUGCCGUAU GCUCCGAGAG ACUUAUUCGU | 2520 |
| CGCGCGAGAA GCACUGCCUU UCGGACGAUA CUCCGUCAAG ACAUUGCUUU CUUUGACAAG | 2580 |
| GAAGAGAAUA GCACCGGCGC UCUGACCUCU UUCCUGUCCA CCGAGACGAA GCAUCUCUCC | 2640 |
| GGUGUUAGCG GUGUGACUCU AGGCACGAUC UUGAUGACCU CCACGACCCU AGGAGCGGCU | 2700 |
| AUCAUUAUUG CCCUGGCGAU UGGGUGGAAA UUGGCCUUAG UUUGUAUCUC GGUUGUGCCG | 2760 |
| GUUCUCCUGG CAUGCGGUUU CUACCGAUUC UAUAUGCUAG CCCAGUUUCA AUCACGCUCC | 2820 |
| AAGCUUGCUU AUGAGGGAUC UGCAAACUUU GCUUGCGAGG CUACAUCGUC UAUCCGCACA | 2880 |
| GUUGCGUCAU UAACCCGGGA AAGGGAUGUC UGGGAGAUUU ACCAUGCCCA GCUUGACGCA | 2940 |
| CAAGGCAGGA CCAGUCUAAU CUCUGUCUUG AGGUCAUCCC UGUUAUAUGC GUCGUCGCAG | 3000 |
| GCACUUGUUU UCUUCUGCGU UGCGCUCGGG UUUUGGUACG GAGGGACACU UCUUGGUCAC | 3060 |
| CACGAGUAUG ACAUUUUCCG CUUCUUUGUU UGUUUCUCCG AGAUUCUCUU UGGUGCUCAA | 3120 |
| UCCGCGGGCA CCGUCUUUUC CUUUGCACCA GACAUGGGCA AGGCGAAGAA UGCGGCCGCC | 3180 |
| GAAUUCCGAC GACUGUUCGA CCGAAAGCCA CAAAUUGAUA ACUGGUCUGA AGAGGGCGAG | 3240 |
| AAGCUCGAAA CGGUGGAAGG UGAAAUCGAA UUUAGGAACG UGCACUUCAG AUACCCGACC | 3300 |
| CGCCCAGAAC AGCCUGUCCU GCGCGGCUUG GACCUGACCG UGAAGCCUGG ACAAUAUGUU | 3360 |
| GCGCUUGUCG GACCCAGCGG UUGUGGCAAG AGUACCACCA UUGCAUUGCU UGAGCGCUUU | 3420 |
| UACGAUGCGA UUGCCGGGUC CAUCCUUGUU GAUGGGAAGG ACAUAAGUAA ACUAAAUAUC | 3480 |
| AACUCCUACC GCAGCUUUCU GUCACUGGUC AGCCAGGAGC CGACACUGUA CCAGGGCACC | 3540 |
| AUCAAGGAAA ACAUCUUACU UGGUAUUGUC GAAGAUGACG UACCGGAAGA AUUCUUGAUU | 3600 |
| AAGGCUUGCA AGGACGCUAA UAUCUACGAC UUCAUCAUGU CGCUCCCGGA GGGCUUUAAU | 3660 |
| ACAGUUGUUG GCAGCAAGGG AGGCAUGUUG UCUGGCGGCC AAAAGCAACG UGUGGCCAUU | 3720 |
| GCCCGAGCCC UUCUUCGGGA UCCCAAAAUC CUUCUUCUCG AUGAAGCGAC GUCAGCCCUC | 3780 |
| GACUCCGAGU CAGAAAAGGU CGUCCAGGCG GCUUUGGAUG CCGCUGCCCG AGGCCGAACC | 3840 |
| ACAAUCGCCG UUGCACACCG ACUCAGCACG AUUCAAAAGG CGGACGUUAU CUAUGUUUUC | 3900 |
| GACCAAGGCA AGAUCGUCGA AAGCGGAACG CACAGCGAAC UGGUCCAGAA AAAGGGCCGG | 3960 |
| UACUACGAGC UGGUCAACUU GCAGAGCUUG GGCAAGGGCC AU | 4002 |